(12) United States Patent
Thompson

(10) Patent No.: US 6,239,328 B1
(45) Date of Patent: *May 29, 2001

(54) METHOD FOR REDUCING EXPRESSION VARIABILITY OF TRANSGENES IN PLANT CELLS

(75) Inventor: William F. Thompson, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 09/089,003

(22) Filed: Jun. 2, 1998

Related U.S. Application Data

(63) Continuation-in-part of application No. 08/424,229, filed on Apr. 19, 1995, now Pat. No. 5,773,689, which is a continuation-in-part of application No. 07/956,420, filed on Oct. 5, 1992, now abandoned.
(60) Provisional application No. 60/048,418, filed on Jun. 3, 1997.

(51) Int. Cl.$^7$ .......................... C12N 15/82; C12N 15/84; A01H 5/00; A01H 5/10
(52) U.S. Cl. ..................... 800/278; 260/294; 260/320; 260/268; 435/468; 435/469; 536/24.1
(58) Field of Search ................................. 800/260, 268, 800/278, 293, 294, 295, 298, 320; 435/320.1, 468, 469, 470; 536/24.1

(56) References Cited

U.S. PATENT DOCUMENTS

| | | | |
|---|---|---|---|
| 5,773,689 | 6/1998 | Thompson et al. | 802/205 |
| 5,773,695 | 6/1998 | Thompson et al. | 800/205 |

FOREIGN PATENT DOCUMENTS

94/07902   4/1994   (WO).

OTHER PUBLICATIONS

Phi–Van et al. Mol. Cell. Biol. 10(5): 2302–2307, May 1990.*

Stief et al. Nature 341: 343–345, Sep. 1989.*

Breyne et al.; Characterization of a Plant Scaffold Attachment Region in a DNA Fragment That Normalizes Transgene Expression in Tobacco, *The Plant Cell*, 4:463–471 (1992).

Clapham et al.; Enhancement of Short– and Medium–term Expression of Transgenes in Embryogenic Suspensions of *Picea Abies* (L.) Karst, *Journal of Experimental Botany*, 46(287):665–662 (1995).

Allen et al.; High–Level Transgene Expression in Plant Cells: Effects of a Strong Scaffold Attachment Region from Tobacco, *The Plant Cell*, 8:899–913 (1996).

Han et al.; Martrix Attachment Regions (MARs) Enhance Transformation Frequency and Transgene Expression in Poplar, *Transgenic Research*, 6:415–420 (1997).

Allen et al.; Scaffold Attachment Regions (SARS) Increase Reporter Gene Expression in Stably Transformed Plant Cells, *Abstract #560, Supplement to Plant Physiology*, 102(1):100 (May 1993).

Allen et al.; Scaffold Attachment Regions Increase Reporter Gene Expression in Stably Transformed Plant Cells, *The Plant Cell*, 5:603–613 (1993).

Liu et al.; The Influences of Two Plant Nuclear Matrix Attachment Regions (MARs) on Gene Expression in Transgenic Plants, *Plant Cell Physiol.*, 39(1):115–123 (Jan. 1998).

* cited by examiner

*Primary Examiner*—David T. Fox
(74) *Attorney, Agent, or Firm*—Myers Bigel Sibley & Sajovec

(57) ABSTRACT

A method of reducing gene silencing, increasing expression, and/or reducing expression variability of foreign DNA in plants or plant cells comprises providing a plant cell capable of regeneration; and then transforming the plant cell with a DNA construct comprising an expression cassette, which construct comprises, in the 5' to 3' direction, a first matrix attachment region, a transcription initiation region, a structural gene positioned downstream from the transcription initiation region and operatively associated therewith, and a second matrix attachment region, wherein the first and second matrix attachment regions are different.

10 Claims, No Drawings

US 6,239,328 B1

METHOD FOR REDUCING EXPRESSION VARIABILITY OF TRANSGENES IN PLANT CELLS

This application is a continuation-in-part of commonly owned copending application Ser. No. 60/048,418, filed Jun. 3, 1997, the disclosure of which is incorporated by reference herein in its entirety, which is a continuation-in-part of commonly owned application Ser. No. 08/424,229, filed Apr. 19, 1995, now issued as U.S. Pat. No. 5,773,689, the disclosure of which is incorporated by reference herein in its entirety, which is in turn a continuation of Ser. No. 07/956,420, filed Oct. 5, 1992, abandoned.

FIELD OF THE INVENTION

The present invention relates to methods for reducing the variability of expression, increasing expression, and/or reducing gene silencing in transgenic plants.

BACKGROUND OF THE INVENTION

Agricultural biotechnology, and particularly plant biotechnology, has become recognized as one of the principal areas for the application of biotechnology techniques. Systems exist for transforming plant cells and regenerating complete plants from the transformed cells; structural gene and gene regulatory regions continue to be identified; and the need for plants with genetically engineered traits such as insect resistance and drought resistance remains strong.

A problem with the expression of foreign genes in plants is the clonal variation in the expression of the same gene in independent transformants: a problem referred to as "position effect" variation. No completely satisfactory method of obviating this problem has yet been developed, and there is accordingly a continued need for solutions to this problem.

L. Mlynarova, *Approaching the Lower Limits of Transgene Variability*, The Plant Cell 8, 1589–1599 (1996) is concerned with Tobacco only. Monocots are neither nor disclosed nor suggested. In addition, Mlynarova is only concerned with an F2 generation produced by selfing the F1 generation.

PCT Application WO94/07902, titled Method for Increasing Expression and Reducing Expression Variability of Foreign Genes in Plant Cells, (published 14 Apr. 1994) it is stated that "where two matrix attachment regions are employed, they may be the same or different." (page 5, lines 13–15).

SUMMARY OF THE INVENTION

A method of reducing gene silencing, increasing expression, and/or reducing expression variability of foreign DNA in plants or plant cells comprises providing a plant cell capable of regeneration; and then transforming said plant cell with a DNA construct comprising an expression cassette, which construct comprises, in the 5' to 3' direction, a first matrix attachment region, a transcription initiation region, a structural gene positioned downstream from said transcription initiation region and operatively associated therewith, and a second matrix attachment region, wherein said first and second matrix attachment regions are different.

In a preferred embodiment of the foregoing, a method of making recombinant plants with reduced silencing of expression, increased expression, and/or reduced expression variability of of foreign genes therein comprises: (a) providing a plant cell, preferably a monocot plant cell, capable of regeneration; (b) transforming the plant cell with a DNA construct comprising an expression cassette, which construct comprises, in the 5' to 3' direction, a transcription initiation region, a structural gene positioned downstream from the transcription initiation region and operatively associated therewith, a first matrix attachment region positioned 5' to the structural gene, and a second matrix attachment region positioned 3' to the structural gene, to produce a transformed plant cell; then (c) propagating a plant from said transformed plant cell to provide a first transgenic plant; and then (d) sexually propagating said first transgenic plant to provide a subsequent transgenic plant having reduced silencing of expression of foreign genes therein. In a preferred embodiment, the plant is a monocot, and the subsequent transgenic plant is a hybrid of one parent that contains the aforesaid expression cassette and another that does not.

A second aspect of the present invention is a DNA construct comprising an expression cassette, which construct comprises, in the 5' to 3' direction, a transcription initiation region, a structural gene positioned downstream from the transcription initiation region and operatively associated therewith, a first AR positioned: 5' to the transcription initiation region and a second MAR positioned 3' to the structural gene, where the first and second MAR are different from one another.

A third aspect of the present invention is a DNA construct as given above carried by a plant transformation vector.

A fourth aspect of the present invention is a plant cell containing a DNA construct as given above.

A fifth aspect of the present invention is a recombinant plant comprising transformed plant cells, the transformed plant cells containing a heterologous DNA construct as given above.

The foregoing and other objects and aspects of this invention are explained in the specification set forth below.

DETAILED DESCRIPTION OF THE INVENTION

The present invention may be carried out with cells from a variety of different plants. As used herein, the term "plant" or "plants" means vascular plants, including both monocots and dicots, and both angiosperms and gymnosperms. Monocots are preferred.

The term "operatively associated," as used herein, refers to DNA sequences on a single DNA. molecule which are associated so that the function of one is affected by the other. Thus, a transcription initiation region is operatively associated with a structural gene when it is capable of affecting the expression of that structural gene (i.e., the structural gene is under the transcriptional control of the transcription initiation region). The transcription initiation region is said to be "upstream" from the structural gene, which is in turn said to be "downstream" from the transcription initiation region.

DNA constructs, or "expression cassettes," of the present invention preferably include, 5' to 3' in the direction of transcription, a transcription initiation region, a structural gene positioned downstream from the transcription initiation region and operatively associated therewith, a MAR positioned: (i) 5' to the transcription initiation region, (ii) 3' to the structural gene, or (iii) both 5' to the transcription initiation region and 3' to the structural gene, and, optionally, a termination sequence including stop signal for RNA polymerase and a polyadenylation signal for polyadenylase (e.g., the nos terminator). The promoter should be capable of operating in the cells to be transformed. The termination region may be derived from the same gene as the promoter region, or may be derived from a different gene.

Matrix attachment regions (MARs; also called scaffold attachment regions, or "SARs") that are used to carry out the present invention may be of any suitable origin. In general, the MAR of any eukaryotic organism (including plants, animals, and yeast) may be employed. See, e.g., G. Allen et al., *The Plant Cell* 5, 603–613 (1993); M. Eva Luderus et al., *Cell* 70, 949–959 (1992); G. Hall et al., *Proc. Natl. Acad. Sci. USA* 88, 9320–9324 (1991). For example, animal MARs are shown to be operational in plants in P. Breyne, *The Plant Cell* 4, 463–471 (1992), and yeast MARs are operational in plants. Plant MARs may be taken from any suitable plant, including those plants specified above and below; animal MARs may be taken from any suitable animal including mammals (e.g., dog, cat), birds (e.g., chicken, turkey), etc.; and MARs may be taken from other eukaryotes such as fungi (e.g., *Saccharomyces cereviceae*). Where two matrix attachment regions are employed, they may be the same or different. The length of the MAR is not critical so long as it retains operability as an SAR, with lengths of from 400 to 1000 base pairs being typical. MARs can be identified and isolated in accordance with known techniques. See, e.g., PCT Application WO94/07902, titled Method for Increasing Expression and Reducing Expression Variability of Foreign Genes in Plant Cells, (published 14 Apr. 1994).

As noted above, the first and second matrix attachment regions are preferably different. In one embodiment, the second matrix attachment region has the same nucleotide sequence as the first matrix attachment region, and is positioned in the DNA in opposite orientation to said first matrix attachment region. In another embodiment, the second matrix attachment region has a different nucleotide sequence from said the matrix attachment region. Matrix attachment regions that differ are those that include some degree of non-homology as will be readily appreciated by those skilled in the art. Any degree of difference may be employed. Difference in homology can be determined by lack of hybridization of the sequences or segments in accordance with known techniques. See, e.g., Sambrook et al., *Molecular Cloning*, eds., Cold Spring Harbor Laboratory Press (1989). For example, hybridization of such sequences may be carried out under conditions of reduced stringency, medium stringency or even stringent conditions (e.g., conditions represented by a wash stringency of 35–40% Formamide with 5×Denhardt's solution, 0.5% SDS and 1×SSPE at 37° C.; conditions represented by a wash stringency of 40–45% Formamide with 5×Denhardt's solution, 0.5% SDS, and 1×SSPE at 42° C.; and conditions represented by a wash stringency of 50% Formamide with 5×Denhardt's solution, 0.5% SDS and 1×SSPE at 42° C., respectively), to DNA encoding resistance to transactivators disclosed herein in a standard hybridization assay. See J. Sambrook et al., *Molecular Cloning, A Laboratory Manual* 2d Ed. (1989) Cold Spring Harbor Laboratory. In general, MARs that are different from one another will be not more than about 98% homologous, 95% homologous, 90% homologous, 80% homologous, or even 70% or 60% homologous or less therewith. That is, the sequence similarity of sequences may range, sharing not more than about 60%, 70%, 80%, and even about 90%, 95%, or 98% or less sequence similarity.

The transcription initiation region, which includes the RNA polymerase binding site (promoter), may be native to the host plant to be transformed or may be derived from an alternative source, where the region is functional in the host plant. Other sources include the Agrobacterium T-DNA genes, such as the transcriptional initiation regions for the biosynthesis of nopaline, octapine, mannopine, or other opine transcriptional initiation regions; transcriptional initiation regions from plants, such as the ubiquitin promoter; root specific promoters (see, e.g., U.S. Pat. No. 5,459,252 to Conkling et al.; WO 91/13992 to Advanced Technologies); transcriptional initiation regions from viruses (including host specific viruses), or partially or wholly synthetic transcription initiation regions. Transcriptional initiation and termination regions are well known (see, e.g., dGreve, *J. Mol. Appl. Genet.* 1, 499–511 (1983); Salomon et al., *EMBO J.* 3, 141–146 (1984); Garfinkel et al., Cell 27, 143–153 (1983); Barker et al., *Plant Mol. Biol.* 2, 235–350 (1983)); including various promoters isolated from plants (see, e.g., U.S. Pat. No. 4,962,028) and viruses (such as the cauliflower mosaic virus promoter, CaMV 35S).

The transcriptional initiation regions may, in addition to the RNA polymerase binding site, include regions which regulate transcription, where the regulation involves, for example, chemical or physical repression or induction (e.g., regulation based on metabolites, light, or other physicochemical factors; see, e.g., WO 93/06710 disclosing a nematode responsive promoter) or regulation based on cell differentiation(such as associated with leaves, roots, seed, or the like in plants; see, e.g., U.S. Pat. No. 5,459,252 disclosing a root-specific promoter). Thus, the transcriptional initiation region, or the regulatory portion of such region, is obtained from an appropriate gene which is so regulated. For example, the 1,5-ribulose biphosphate carboxylase gene is light-induced and may be used for transcriptional initiation. Other genes are known which are induced by stress, temperature, wounding, pathogen effects, etc.

The term "structural gene" herein refers to those portions of genes which comprise a DNA segment coding for a protein, polypeptide, or portion thereof, possibly including a ribosome binding site and/or a translational start codon, but lacking a transcription initiation region. The term can also refer to copies of a structural gene naturally found within a cell but artificially introduced. The structural gene may encode a protein not normally found in the plant cell in which the gene is introduced or in combination with the transcription initiation region to which it is operationally associated, in which case it is termed a heterologous structural gene. Genes which may be operationally associated with a transcription initiation region of the present invention for expression in a plant species may be derived from a chromosomal gene, cDNA, a synthetic gene, or combinations thereof. Any structural gene may be employed. The structural gene may encode an enzyme to introduce a desired trait into the plant, such as glyphosphate resistance; the structural gene may encode a protein such as a *Bacillus thuringiensis* protein (or fragment thereof to impart insect resistance to the plant; the structural gene may encode a plant virus protein or fragment thereof to impart virus resistance to the plant. The term "structural gene" as used herein is also intended to encompass a DNA encoding an antisense agent that will bind to a particular mRNA in the plant cell and downregulate translation thereof. See, e.g., U.S. Pat. No. 5,107,065 to Shewmaker et al.

Expression cassettes useful in methods of the present invention may be provided in a DNA construct which also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly a plant host. The markers may be protection against a biocide, such as antibiotics, toxins, heavy metals, or the like; provide complementation, for example by imparting prototrophy to an auxotrophic host; or provide a visible phenotype through the production of a novel compound. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are β-glucuronidase, providing indigo production; luciferase, providing visible light production; NPTII, providing kanamycin resistance or G418 resistance; HPT, providing hygromycin resistance; and the mutated aroA gene, providing glyphosate resistance.

The various fragments comprising the various constructs, expression cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature and find particular exemplification in Sambrook et al., *Molecular Cloning: A Laboratory Manual*, (2d Ed. 1989)(Cold Spring Harbor Laboratory, Cold Spring Harbor, N.Y.).

As used herein, a transgenic plant refers to a plant in which at least some cells are stably transformed with a heterologous DNA construct. As used herein, a heterologous DNA construct refers to DNA which is artificially introduced into a cell or into a cell's ancestor. Such DNA may contain genes or DNA which would not normally be found in the cell to be transformed, or may contain genes or DNA which is contained in the cell to be transformed. In the latter case, cells are transformed so that they contain additional or multiple copies of the DNA sequence or gene of interest.

Vectors which may be used to transform plant tissue with DNA constructs of the present invention include Agrobacterium vectors, non-Agrobacterium vectors (particularly ballistic vectors), as well as other known vectors suitable for DNA-mediated transformation. Agrobacterium vectors are preferred.

Microparticles carrying a DNA construct of the present invention, which microparticles are suitable for the ballistic transformation of a cell, are useful for transforming cells according to the present invention. The microparticle is propelled into a cell to produce a transformed cell. Where the transformed cell is a plant cell, a plant may be regenerated from the transformed cell according to techniques known in the art. Any suitable ballistic cell transformation methodology and apparatus can be used in practicing the present invention. Exemplary apparatus and procedures are disclosed in Stomp et al., U.S. Pat. No. 5,122,466; and Sanford and Wolf, U.S. Pat. No. 4,945,050 (the disclosures of all U.S. Patent references cited herein are incorporated herein by reference in their entirety). When using ballistic transformation procedures, the expression cassette may be incorporated into a plasmid capable of replicating in the cell to be transformed. Examples of microparticles suitable for use in such systems include 1 to 5 μm gold spheres. The DNA construct may be deposited on the microparticle by any suitable technique, such as by precipitation. Such ballistic transformation techniques are useful for introducing foreign genes into a variety of plant species, and are particularly useful for the transformation of monocots.

Vectors that may be used to carry out the present invention include Agrobacterium vectors. Numerous Agrobacterium vectors are known. See, e.g, U.S. Pat. No. 4,536,475 to Anderson; U.S. Pat. No. 4,693,977 to Schliperoort et al.; U.S. Pat. No. 4,886,937 to Sederoff et al.; U.S. Pat. No. 5,501,967 To Offringa et al.; T. Hall et al., EPO Application No. 0122791; R. Fraley et al., *Proc. Natl. Acad. Sci. USA* 84:4803 (1983); L. Herrera-Estrella et al., *EMBO J*. 2:987 (1983); G. Helmer et al., *Bio/Technology* 2:520 (1984); N. Murai et al., *Science* 222:476 (1983). In general, such vectors comprise an agrobacteria, typically *Agrobacterium tumefaciens*, that carried at least one tumor-inducing (or "Ti") plasmid. When the agrobacteria is *Agrobacterium rhizogenes*, this plasmid is also known as the root-inducing (or "Ri") plasmid. The Ti (or Ri) plasmid contains DNA referred to as "T-DNA" that is transferred to the cells of a host plant when that plant is infected by the agrobacteria. In an Agrobacterium vector, the T-DNA is modified by genetic engineering techniques to contain the "expression cassette", or the gene or genes of interest to be expressed in the transformed plant cells, along with the associated regulatory sequences. The agrobacteria may contain multiple plasmids, as in the case of a "binary" vector system. Such Agrobacterium vectors are useful for introducing foreign genes into a variety of plant species, and are particularly useful for the transformation of dicots.

The combined use of Agrobacterium vectors and microprojectile bombardment is also known in the art (see, e.g European Patent Nos. 486233 and 486234 to D. Bidney). Transgenic plants may be produced using the DNA constructs of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants (the term "subsequent generation" as used herein refers to T2 generation or thereafter where), and the T2 plants further propagated through classical breeding techniques. Where the transgenic plant is bred with a plant that does not carry the same expression cassette to produce a hybrid plant, either plant may be the male of female parent. A dominant selectable marker (such as npt II) can be associated with the expression cassette to assist in breeding. Seeds may be collected from mature plants of the present invention in accordance with conventional techniques to provide seed that germinates into a plant as described herein.

Plants which may be employed in practicing the present invention include (but are not limited to) tobacco (*Nicotiana tabacum*), potato (*Solanum tuberosum*), soybean (*glycine max*), peanuts (*Arachis hypogaea*), cotton (*Gossypium hirsutum*), sweet potato (*Ipomoea batatus*), cassava (*Manihot esculenta*), coffee (Cofea spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), corn (*Zea mays*, also known as maize), wheat, oats, rye, barley, rice, vegetables, ornamentals, and conifers. Vegetables include tomatoes (*Lycopersicon esculentum*), lettuce (e.g., *Lactuea sativa*), green beans (*Phaseolus vulgaris*), lima beans (*Phaseolus limensis*), peas (Pisum spp.) and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (*Tulipa* spp.), daffodils (Narcissus spp.), petunias (*Petunia hybrida*), carnation (*dianthus caryophyllus*), poinsettia (*Euphorbia pulcherima*), and chrysanthemum. Gymnosperms which may be employed to carrying out the present invention include conifers, including pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

The foregoing examples are illustrative of the present invention, and are not to be construed as limiting thereof. The invention is defined by the following claims, with equivalents of the claims to be included therein.

That which is claimed is:

1. A method of making recombinant plants with reduced silencing of expression of foreign genes therein, comprising:
    (a) providing a monocot plant cell capable of regeneration;
    (b) transforming, the plant cell with a DNA construct comprising an expression cassette, which construct comprises, in the 5' to 3' direction, a transcription initiation region, a structural gene positioned downstream from the transcription initiation region and operatively associated therewith, a first matrix attachment region positioned 5' to the structural gene, and a second matrix attachment region positioned 3' to the structural gene, to produce a transformed plant cell; then
    (c) propagating a plant from said transformed plant cell to provide a first transgenic plant; and then
    (d) sexually propagating said first transgenic plant to provide a subsequent transgenic plant having reduced silencing of expression of foreign genes therein.

2. A method according to claim 1, wherein said subsequent transgenic plant is a hybrid plant that is homozygous for said structural gene.

3. A method according to claim 2, wherein said first transgenic plant is the male parent of said hybrid plant.

4. A method according to claim 2, wherein said first transgenic plant is the female parent of said hybrid plant.

5. A method according to claim 1, wherein said second matrix attachment region has the same nucleotide sequence as said first matrix attachment region, and is positioned in said DNA in opposite orientation to said first matrix attachment region.

6. A method according to claim 1, wherein said second matrix attachment region has a different nucleotide sequence from said first matrix attachment region.

7. A method according to claim 1, wherein said transformation step is an Agrobacterium-mediated transformation step.

8. A plant produced by the method of claim 1.

9. A hybrid plant produced by the method of claim 1.

10. A seed that germinates into a plant produced by the method of claim 1.

* * * * *